United States Patent [19]

Brown, deceased et al.

[11] 3,997,324
[45] Dec. 14, 1976

[54] HERBICIDAL N- OXYTHIO-SUBSTITUTED UREAS

[75] Inventors: Melancthon S. Brown, deceased, late of Berkeley, Calif., by Gustave K. Kohn, special administrator; Gustave K. Kohn, Berkeley, Calif.

[73] Assignee: Chevron Research Company, San Francisco, Calif.

[22] Filed: Aug. 29, 1975

[21] Appl. No.: 608,866

Related U.S. Application Data

[60] Division of Ser. No. 483,583, July 11, 1974, Pat. No. 3,928,407, which is a continuation-in-part of Ser. No. 250,907, May 8, 1972, Pat. No. 3,853,966, which is a continuation-in-part of Ser. No. 189,732, Oct. 15, 1971, abandoned, which is a continuation-in-part of Ser. No. 88,212, Nov. 9, 1970, Pat. No. 3,755,437, and Ser. No. 88,105, Nov. 9, 1970, Pat. No. 3,679,733.

[52] U.S. Cl. ................................................. 71/98
[51] Int. Cl.$^2$ ........................................... A01N 9/12
[58] Field of Search ...................... 71/98; 260/453 R

[56] References Cited
UNITED STATES PATENTS 2,717,828  9/1955   Birum et al. ........................... 71/98
3,711,530  1/1973   Kobzina et al. ........................ 71/98
3,812,209  5/1974   Brown .................................... 71/98
3,824,281  7/1974   Brown .................................... 71/98
3,853,966  12/1974  Brown .................................... 71/98
3,857,883  12/1974  Cleveland .............................. 71/98

*Primary Examiner*—Glennon H. Hollrah
*Attorney, Agent, or Firm*—G. F. Magdeburger; D. A. Newell; Raymond Owyang

[57] ABSTRACT

Herbicidal oxythio-substituted ureas of the formula:

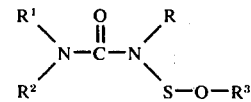

wherein R, R$^1$ and R$^2$ individually are hydrogen, alkyl, cycloalkyl, bicycloalkyl, alkoxy or aryl, and R$^3$ is alkyl, cycloalkyl, bicycloalkyl or aryl. The oxythio-substituted ureas are prepared by reacting an N-chlorothio urea and a hydroxylic compound.

30 Claims, No Drawings

HERBICIDAL N- OXYTHIO-SUBSTITUTED UREAS

CROSS-REFERENCE TO RELATED APPLICATIONS

This application is a division of application Ser. No. 483,583, filed July 11, 1974, now U.S. Pat. No. 3,928,407, which is a continuation-in-part of application Ser. No. 250,907, filed May 8, 1972, now U.S. Pat. No. 3,853,966, which in turn is a continuation-in-part of application Ser. No. 189,732 filed Oct. 15, 1971, now abandoned, which in turn is a continuation-in-part of Ser. Nos. 88,212, filed November 9, 1970, now U.S. Pat. No. 3,755,437, and 88,105, filed November 9, 1970, now U.S. Pat. No. 3,679,733. The disclosures of Ser. Nos. 250,907, 189,732 and 88,212 are incorporated by reference.

DESCRIPTION OF THE PRIOR ART

German Pat. No. 2,045,440, published Mar. 23, 1972, discloses triorgano-substituted chlorothio ureas.

E. Kuhle, Synthesis, 617 (1971), discloses the reaction of sulfenyl halides with hydroxylic compounds to produce monothioperoxide compounds.

U.S. Pat. Nos. 3,539,538 and 3,812,209 disclose dithiosubstituted ureas.

DESCRIPTION OF THE INVENTION

The oxythio-substituted ureas of the invention are represented by the formula (I):

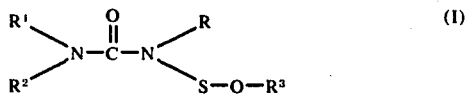

wherein R, $R^1$ and $R^2$ individually are alkyl of 1 to 6 carbon atoms, cycloalkyl or bicycloalkyl of up to 10 carbon atoms, alkoxy of 1 to 4 carbon atoms or carbocyclic mononuclear or binuclear aryl of 6 to 12 carbon atoms substituted with up to 2 (0 to 2) of the same or different substituents selected from fluorine, chlorine, bromine, nitro, trifluoromethyl or alkoxy of 1 to 4 carbon atoms and $R^3$ is alkyl of 1 to 10 carbon atoms, cycloalkyl or bicycloalkyl of up to 10 carbon atoms or carbocyclic mononuclear or binuclear aryl of 6 to 12 carbon atoms substituted with up to 2 (0 to 2) fluorine, chlorine, bromine, nitro, trifluoromethyl, or alkoxy of 1 to 4 carbon atoms.

Representative alkyl groups which R, $R^1$ and $R^2$ may represent include methyl, ethyl, n-propyl, isopropyl, n-butyl, t-butyl, n-pentyl and n-hexyl. The preferred alkyl group is methyl.

Representative alkoxy groups which R, $R^1$ and $R^2$ may represent include methoxy, ethoxy, propoxy and butoxy.

Representative cycloalkyl and bicycloalkyl groups which R, $R^1$ and $R^2$ may represent include cyclopropyl, cyclopentyl, cyclohexyl, 4-methylcyclohexyl, bicyclo[3.2.0]heptyl, bicyclo[2.2.1]heptyl, bicyclo[3.3.-0]octyl, and bicyclo[4.2.0]octyl. The cycloalkyl groups preferably have 5 to 6 carbon atoms and the bicycloalkyl groups preferably have 6 to 10 carbon atoms.

Representative hydrocarbyl aryl groups which R, $R^1$ and $R^2$ may represent include phenyl; naphthyl, alkylphenyl of 7 to 12 carbon atoms such as 2-methylphenyl, 3-methylphenyl, 4-ethylphenyl, 2,4-dimethylphenyl, 3,4-dimethylphenyl, 3-secbutylphenyl; and phenylalkyl of 7 to 12 carbon atoms such as benzyl, 3-phenylpropyl, and 4-phenylbutyl.

Representative substituted aryl groups which R, $R^1$ and $R^2$ may represent include phenyl, phenylalkyl and alkylphenyl substituted with 1 to 2 fluorine, chlorine, bromine, trifluoromethyl, nitro or alkoxy of 1 to 4 carbon atoms, such as 2-fluorophenyl, 4-fluorophenyl, 2-chlorophenyl, 3-chlorophenyl, 3,4-dichlorophenyl, 4-trifluoromethylphenyl, 3-chloro-4-bromophenyl, 2-chloro-4-methylphenyl, 2-fluoro-4-methylphenyl, 4-chlorobenzyl, 4-fluorobenzyl, 2-(2-fluorophenyl)ethyl, 4-methoxyphenyl, 4-ethoxyphenyl, 4-methoxy-2-methylphenyl, 4-methoxybenzyl, 2-nitrophenyl, 4-nitrophenyl and 4-nitrobenzyl, 2-methoxy-4-chlorophenyl and 2-chloro-4-nitrophenyl. Preferred substituted aryl groups are halo-substituted phenyls, especially those having 1 to 2 fluorine or chlorine substituents.

Representative alkyl $R^3$ groups are methyl, ethyl, isopropyl, n-butyl, isopentyl, hexyl, octyl and decyl.

Representative cycloalkyl $R^3$ groups are cyclopropyl, cyclopentyl, cyclohexyl, 2-methylcyclohexyl, 4-methylcyclohexyl, cycloheptyl, and cyclooctyl; and representative bicycloalkyl $R^3$ groups are bicyclo[3.2.0]heptyl, bicyclo[2.2.1]heptyl, bicyclo[3.3.0]octyl, bicyclo[4.2.0]octyl, bicyclo[3.3.0]octyl, and bicyclo[3.2.-1]octyl. Cycloalkyl $R^3$ groups preferably have 5 to 6 carbon atoms and bicycloalkyl $R^3$ groups preferably have 6 to 10 carbon atoms.

Representative aryl $R^3$ groups include hydrocarbyl aryl groups such as phenyl, naphthyl, phenylalkyl of 7 to 12 carbon atoms such as benzyl and 3-phenylpropyl, and phenylalkyl of 7 to 12 carbon atoms such as tolyl, xylyl, 3,4,5-trimethylphenyl, and 2,4-diethylphenyl. Representative substituted-aryl $R^3$ groups include phenyl, phenylalkyl and alkylphenyl substituted with 1 to 2 fluorine, chlorine, bromine, trifluoromethyl, nitro or alkoxy of 1 to 4 carbon atoms, such as 2-fluorophenyl, 3,4-dichlorophenyl, 4-bromophenyl, 2-methyl-4-chlorophenyl, 2-trifluoromethylphenyl, 4-nitrophenyl, and 3-methoxyphenyl.

R preferably is alkyl of 1 to 6 carbon atoms.

$R^1$ preferably is phenyl, naphthyl, alkylphenyl of 7 to 12 carbon atoms, phenylalkyl of 7 to 12 carbon atoms, or phenyl, alkylphenyl or phenylalkyl substituted on the phenyl ring with 1 to 2 fluorine, chlorine, bromine, trifluoromethyl, nitro or alkoxy of 1 to 4 carbon atoms. $R^1$ most preferably is phenyl or alkylphenyl substituted with 1 to 2 fluorine, chlorine or bromine.

$R^2$ preferably is hydrogen.

$R^3$ preferably is alkyl of 1 to 10 carbon atoms, cycloalkyl or bicycloalkyl of up to 10 carbon atoms, or phenyl or phenyl substituted with 1 to 2 fluorine, chlorine or bromine. $R^3$ most preferably is alkyl, cycloalkyl of 5 to 6 carbon atoms or bicycloalkyl of 6 to 10 carbon atoms.

A preferred class of urea compounds of formula (I) is that wherein at least one R, $R^1$ or $R^2$ group is hydrogen and $R^3$ is as defined above.

Another preferred class of urea compounds of formula (I) is that wherein R is alkyl and $R^2$ is hydrogen, and $R^1$ and $R^3$ are as defined above.

Another preferred class of urea compounds of formula (I) is that wherein R is alkyl, $R^2$ is hydrogen, and $R^1$ is carbocyclic mononuclear or binuclear aryl as defined above.

The most preferred class of urea compounds of formula (I) is that wherein R is alkyl, $R^2$ is hydrogen, $R^1$ is phenyl, alkylphenyl of 7 to 12 carbon atoms, or phenyl or alkylphenyl substituted with 1 to 2 fluorine, chlorine or bromine.

Representative oxythio ureas of formula (I) are:
N-methoxythio urea,
N-ethoxythio-N-methyl urea,
N-propoxythio-N,N'-dimethyl urea,
N-cyclohexoxythio-N-methyl-N',N'-dimethyl urea,
N-methoxythio-N-methyl-N'-cyclohexyl urea,
N-methoxythio-N'-methyl, N,N'-dimethoxy urea,
N-phenoxythio-N-butyl-N'-benzyl urea,
N-benzyloxythio-N-methyl-N'-(2-fluorophenyl) urea
N-methoxythio-N-methyl-N'-(3,4-dichlorophenyl) urea,
N-ethoxythio-N-(3-trifluoromethylphenyl)-N',N'-dimethyl urea,
N-p-methylphenoxythio-N-phenyl-N',N'-dimethyl urea,
N-butoxythio-N-(3,4-dichlorophenyl)-N'-methoxy-N'-methyl urea,
N-norbornyloxythio-N-(3-chloro-4-bromophenyl)-N'-methoxy-N'-methyl urea,
N-methoxythio-N'-(4-bromophenyl)-N,N'-dimethoxy urea,
N-cyclopentoxythio-N-(4-chlorophenyl)-N',N'-dimethyl urea,
N-hexoxythio-N-methyl-N'-(4-nitrophenyl)-N'-methyl urea,
N-phenoxythio-N-methyl-N'-(4-methoxyphenyl)-N'-methyl urea, and
N-decyloxythio-N-(2-methylphenyl)-N',N'-dimethyl urea.

The oxythio urea compounds of formula (I) are prepared in accordance with the following reaction (1):

pound (III) generally varies from about 1.5:1 to 1:1.5, although molar ratios of (II) to (III) of about 1.2:1 to 1:1.2 are preferred. The molar ratios of acid acceptor to the N-chlorothio urea reactant are also substantially equimolar, e.g., the molar ratio of acid acceptor to N-chlorothio urea reactant varies from about 1.5:1 to 1:1.5, although molar ratios of acid acceptor to N-chlorothio urea reactant of about 1.2:1 to 1:1.2 are preferred.

The reaction is generally accomplished by reacting the N-chlorothio urea reactant (II) and the hydroxylic compound (III) in the presence of the acid acceptor in the liquid phase in an inert diluent. Suitable inert diluents for the reaction include alkanes of 5 to 10 carbon atoms, such as hexane, isooctane and decane; aromatic compounds such as benzene and chlorobenzene; oxygenated hydrocarbons such as acyclic alkyl ethers, e.g., dimethoxyethane and dibutyl ether; and cycloalkyl ethers, e.g., dioxane, tetrahydrofuran and tetrahydropyran. Other suitable diluents include nitriles such as acetonitrile and propionitrile; dialkylamides such as dimethylformamide and dialkylsulfoxides such as dimethylsulfoxide. Preferred diluents are chlorinated hydrocarbons of 1 to 2 carbon atoms such as methylene dichloride, chloroform, carbon tetrachloride and ethylene dichloride. Generally the amount of diluent employed ranges from 1 to 50 mols per mol of N-chlorothio urea reactant.

The reaction is suitably conducted at a temperature between $-20°$ C. and the boiling point of the diluent, although temperatures between $0°$ and $50°$ C. are preferred. The reaction is conducted at or above atmospheric pressure.

The urea product (I) is recovered and purified by conventional procedures such as extraction, crystallization, chromatography, etc.

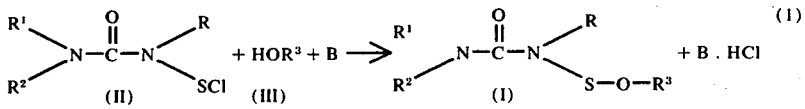

wherein R, $R^1$, $R^2$ and $R^3$ are as defined above, and B is an acid acceptor.

The N-chlorothio urea reactant (II) is prepared in accordance with the following reaction (2):

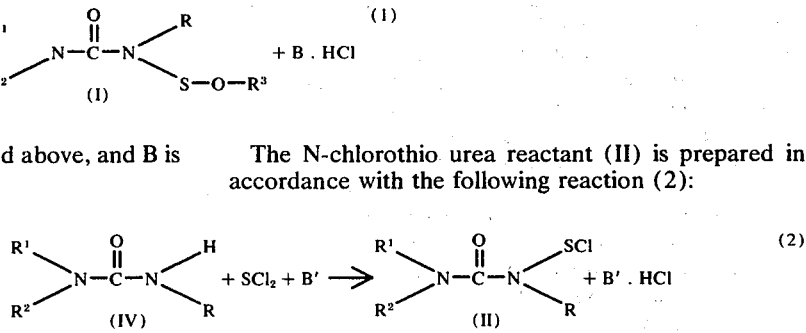

wherein R, $R^1$ and $R^2$ are as defined above and B' is an acid acceptor.

The acid acceptor is an organic base such as a pyridine compound or a trialkylamine compound. Suitable pyridine compounds are pyridine and pyridine compounds of 6 to 10 carbon atoms and of 1 to 2 alkyl groups such as 2-methylpyridine, 2-ethylpyridine, 3-methylpyridine, 3,5-dimethylpyridine, and 2-butylpyridine. Suitable trialkylamines are those wherein the alkyl group contains individually 1 to 4 carbon atoms, such as trimethylamine, triethylamine, tripropylamine and tributylamine.

Generally, commercially available sulfur dichloride of reasonable purity, e.g., greater than 90-98% purity, is suitably employed. The sulfur dichloride may contain small amounts of an inhibitor such as tributylphosphate or triethylphosphate.

The acid acceptor is an inorganic base, e.g., alkali metal hydroxide, bicarbonate or carbonate, or an organic nitrogen base having no N-H group, such as a pyridine compound or a trialkylamine. Suitable pyridine compounds are pyridine and pyridine compounds of 6 to 10 carbon atoms and of 1 to 2 alkyl groups such as 2-methylpyridine, 2-ethylpyridine, 3-methylpyridine, 3,5-dimethylpyridine, and 2-butylpyridine. Suitable trialkylamines are those wherein the alkyl group contains individually 1 to 4 carbon atoms, such as trimethylamine, triethylamine, tripropylamine and tributylamine. The preferred acid acceptors are pyridine compounds, especially pyridine.

The N-chlorothio urea reactant (II) and the hydroxylic compound (III) are employed in substantially equimolar amounts, e.g., the molar ratio of the N-chlorothio urea reactant (II) to the hydroxylic com- The sulfur dichloride and the urea compound are employed in substantially equimolar amounts, e.g., the molar ratio of sulfur dichloride to the urea compound generally varies from about 1.5:1 to 1:1.5, although molar ratios of sulfur dichloride to the urea compound of 1.4:1 to 1.1:1 are preferred. The molar ratio of acid acceptor to sulfur dichloride is also substantially equimolar, e.g., the molar ratio of acid acceptor to sulfur dichloride varies from about 1.2:1 to 1:1.2, although molar ratios of acid acceptor to sulfur dichloride of 1:1 to 1:1.2 are preferred.

In general, the reaction is accomplished by reacting the urea and the sulfur dichloride in the presence of the acid acceptor compound in an inert diluent. The reaction is suitably conducted by adding the sulfur dichloride to a mixture of the urea and the acid acceptor in an inert diluent. Alternatively, the reaction is conducted by adding a mixture of the urea and acid acceptor to a solution of the sulfur dichloride in an inert diluent. However, the preferred method for conducting the reaction comprises reacting the urea and sulfur dichloride in the presence of a limited amount of free uncomplexed acid acceptor. This is suitably accomplished by the addition of the acid acceptor to a substantially equimolar mixture of the urea and the sulfur dichloride so that the mols of free acid acceptor to the total mols of urea reactant and N-chlorothio urea product is less than 0.2:1, preferably less than 0.1:1, and more preferably less than 0.05:1. In other words, during the course of the reaction between the sulfur dichloride and the urea reactant, there should be at least 5 mols of the urea reactant and the N-chlorothio urea product per mol of acid acceptor which is not complexed with hydrochloric acid. Provided that the reaction is conducted with the restricted amount of acid acceptor indicated above, the contacting of the acid acceptor with the mixture of the urea and the sulfur dichloride can be conducted by a variety of procedures. In one modification, the acid acceptor is added in increments, e.g., dropwise, in an inert diluent, if desired, to a mixture of the urea and sulfur dichloride in an inert diluent. In another modification, the acid acceptor is added continuously to a mixture of the urea and sulfur dichloride in an inert diluent.

Suitable inert diluents for the reaction include alkanes of 5 to 10 carbon atoms, such as hexane, isooctane and decane; aromatic compounds such as benzene and chlorobenzene; oxygenated hydrocarbons such as acyclic alkyl ethers, e.g., dimethoxyethane and dibutyl ether; and cycloalkyl ethers, e.g., dioxane, tetrahydrofuran and tetrahydropyran. Other suitable diluents include nitriles such as acetonitrile and propionitrile; dialkylamide such as dimethylformamide and dialkysulfoxides such as dimethylsulfoxide. Preferred diluents are chlorinated hydrocarbons of 1 to 2 carbon atoms, such as methylene dichloride, chloroform, carbon tetrachloride and ethylene dichloride. Generally, the amount of diluent employed ranges from 1 to 50 mols per mol of sulfur dichloride.

The reaction is suitably conducted at a temperature between −20° C. and the boiling point of the diluent, although temperatures between 0° C. and 50° C. are preferred. The reaction is conducted at or above atmospheric pressure.

It is appreciated, of course, that the N-chlorothio urea product of the invention is formed by the substitution of a hydrogen substituent on a urea nitrogen by a sulfenyl chloride group. When the urea reactant has more than one hydrogen substituted on a urea nitrogen, a mixture of monochlorothio derivatives is therefore generally formed (unless the urea reactant is symmetrical, i.e., one $R^1$ or $R^2$ is hydrogen and the other $R^1$ or $R^2$ is the same as R). However, it has been found that when one R, $R^1$ or $R^2$ group is alkyl, the urea compound is preferentially sulfenylated at the nitrogen atom bearing the alkyl group.

The preparation of the oxythio ureas of the invention is illustrated by the following examples.

EXAMPLES

EXAMPLE 1

Preparation of N-chlorothio-N-methyl-N'-2-fluorophenyl urea

A 5.7-g (0.055 mol) sample of sulfur dichloride was added dropwise to a mixture of 8.4 g (0.05 mol) N-methyl-N'-2-fluorophenyl urea and 4.7 g (0.06 mol) pyridine in 50 ml methylene chloride cooled in an ice bath. After the completion of the addition, the pyridine hydrochloride formed during the reaction was filtered. Hexane was added to the filtrate to precipitate some additional pyridine hydrochloride, which was removed by filtration. Evaporation of the resulting filtrate gave a clear red oil. The nuclear magnetic resonance (NMR) spectrum of the oil showed an N-methyl singlet at 3.5 ppm (relative to tetramethylsilane). Elemental analysis showed: %S, calc. 13.6, found 13.6; %Cl, calc. 16.1, found 15.4.

EXAMPLE 2

Preparation of N-chlorothio-N-(3,4-dichlorophenyl)-N',N'-dimethyl urea

A 5.7-g (0.055 mol) sample of sulfur dichloride was added dropwise to a mixture of 11.7 g (0.05 mol) of N-3,4-dichlorophenyl-N',N'-dimethyl urea and 4.7 g (0.06 mol) pyridine in 50 ml methylene chloride cooled in an ice bath. After the completion of the addition, the pyridine hydrochloride was filtered. Hexane was added to precipitate additional pyridine hydrochloride, which was removed by filtration. Evaporation of the resulting filtrate gave the product as a clear yellow oil. The NMR spectrum showed an N',N'-dimethyl singlet at 3.0 ppm (relative to tetramethylsilane). Elemental analysis showed: %S, calc. 10.7, found 10.7; %Cl, calc. 35.6, found 35.4; %C, calc. 36.1, found 36.4; %H, calc. 3.0, found 3.2; %N, calc. 9.3, found 8.7.

EXAMPLE 3

Preparation of N-chlorothio-N-methyl-N'-3,4-dichlorophenyl) urea

A 9.48-g (0.12 mol) sample of pyridine was added dropwise to a slurry of 21.9 g (0.1 mol) N-methyl-N'-(3,4-dichlorophenyl) urea and 11.3 g (0.11 mol) sulfur dichloride in 100 ml methylene dichloride at 25°–30° C. After completion of the addition, pyridine hydrochloride was filtered from the reaction mixture. The NMR spectrum of the reaction mixture showed a singlet at 3.5 ppm (relative to tetramethylsilane) for the N-methyl group of the N-chlorothio-N-methyl-N'-3,4-dichlorophenyl urea product.

EXAMPLE 4

Preparation of N-chlorothio-N,N'-dimethyl urea

Pyridine (9.48 g, 0.12 mol) was added dropwise to a solution of 8.8 g (0.1 mol) N,N'-dimethyl urea and 11.3 g (0.11 mol) sulfur dichloride at 25°–30° C. Pyridine hydrochloride was then filtered from the reaction mixture to give a solution of the N-chlorothio urea product in methylene chloride. The NMR spectrum of the product showed a singlet at 3.5 ppm for the N-methyl group and a doublet at 2.95 ppm for the N'-methyl group.

EXAMPLE 5

Preparation of N-propoxythio-N-methyl-N'-3,4-dichlorophenyl urea

To a solution of about 0.1 mol of N-chlorothio-N-methyl-N'-3,4-dichlorophenyl urea in methylene dichloride, prepared as described in Example 3, was added dropwise a solution of 6 g (0.1 mol) n-propanol and 9.5 g (0.12 mol) pyridine in 20 ml of methylene chloride at 0° C. After completion of the addition, the resulting reaction mixture was stirred in an ice bath for about 10 minutes, washed with water, washed with sodium bicarbonate solution, dried over magnesium sulfate and evaporated under reduced pressure to give 22.6 g of a dark oil residue. The oil residue was purified by column chromatography on silica gel (hexane/chloroform eluant) to give the product as a white, low-melting solid (<25° C.). Elemental analysis showed: %S, calc. 10.4, found 10.4; %C, calc. 23.0, found 22.8.

The product is tabulated in Table I. By a similar procedure, the other oxythio urea compounds tabulated in Table I were prepared.

EXAMPLE 6

Herbicidal Tests

The oxythio urea compounds of the invention are, in general, herbicidal in both pre- and post-emergent applications. For pre-emergent control of undesirable vegetation, these ureas will be applied in herbicidal quantities to the locus or environment of said vegetation, e.g., soil infested with seeds and/or seedlings of such vegetation. Such application will inhibit the growth of or kill the seeds, germinating seeds and seedlings. For post-emergent applications, the oxythio urea compounds will be applied directly to the foliage and other plant parts. Generally they are effective against weed grasses as well as broadleaved weeds. Some may be selective with respect to type of application and/or type of weed.

The urea compounds of the present invention can be used alone as herbicides. However, it is generally desirable to apply the compounds in herbicidal compositions comprising one or more of the herbicidal compounds intimately admixed with a biologically inert carrier. The carrier may be a liquid diluent or a solid, e.g., in the form of dust powder or granules. In the herbicidal composition, the active herbicidal compounds can be from about 0.01 to 95% by weight of the entire composition.

Suitable liquid diluent carriers include water and organic solvents, e.g., hydrocarbons such as benzene, toluene, kerosene, diesel oil, fuel oil, and petroleum naphtha. Suitable solid carriers are natural clays such as kaolinite, atalpulgite and montmorillonite. In addition, talcs, pyrophillite, diatomaceous silica, synthetic fine silicas, calcium aluminosilicate and tricalcium phosphate are suitable carriers. Organic materials such as walnut-shell flour, cottonseed hulls, wheat flour, wood flour or redwood-bark flour may also be used as solid carriers.

The herbicidal composition will also usually contain a minor amount of a surface-active agent. Such surface agents are those commonly known as wetting agents, dispersing agents and emulsifying agents, and can be anionic, cationic or nonionic in character. The herbicidal compositions may also contain other pesticides, adjuvants, stabilizers, conditioners, fillers and the like.

The amount of herbicidal compound or composition administered will vary with the particular plant part or plant growth medium which is to be contacted, the general location of application — i.e., sheltered areas such as greenhouses, as compared to exposed areas such as fields — as well as the desired type of control. Generally, for both pre- and post-emergent control, the herbicidal compounds of the invention are applied at rates of 2 to 60 kg/ha, and the preferred rate is in the range 5 to 40 kg/ha.

Pre- and post-emergent herbicidal tests on the urea compounds tabulated in Table I were made using the following methods:

Pre-Emergent Test

An acetone solution of the test urea compound was prepared by mixing 750 mg urea, 220 mg of a nonionic surfactant and 25 ml of acetone. This solution was added to approximately 125 ml of water containing 156 mg of surfactant.

Seeds of the test vegetation were planted in a pot of soil and the urea solution was sprayed uniformly onto the soil surface at a dose of 33 mcg/cm$^2$. The pot was watered and placed in a greenhouse. The pot was watered intermittently and was observed for seedling emergence, health of emerging seedlings, etc., for a 3-week period. At the end of this period, the herbicidal effectiveness of the urea was rated based on the physiological observations. A 0-to-100 scale was used, 0 representing to phytotoxicity and 100 representing complete kill.

Post-Emergent Test

The test urea compound was formulated in the same manner described above for the pre-emergent test. The concentration of the urea in this formulation was 5000 ppm. This formulation was uniformly sprayed on two similar pots of 24-day-old plants (approximately 15 to 25 plants per pot) at a dose of 33 mcg/cm$^2$. After the plants had dried, they were placed in a greenhouse and then watered intermittently at their bases as needed. The plants were observed periodically for phytotoxic effects and physiological and morphological responses to the treatment. After 3 weeks, the herbicidal effectiveness of the urea was rated based on these observations. A 0-to-100 scale was used, 0 representing no phytotoxicity, 100 representing complete kill.

The results of these tests appear in Table II.

TABLE I

MONOTHIOPEROXY UREA COMPOUNDS

| Compound | Melting Point, °C. | %S Calc. | %S Found | %Cl Calc. | %Cl Found | %N Calc. | %N Found |
|---|---|---|---|---|---|---|---|
| (1) N-propoxythio-N-methyl-N'-(3,4-dichlorophenyl) urea | <25 | 10.4 | 10.4 | — | — | 23.0* | 22.8* |
| (2) N-octoxythio-N-methyl-N'-(3,4-dichlorophenyl) urea | Oil | 8.1 | 8.1 | 18.1 | 17.3 | — | — |
| (3) N-methoxythio-N-methyl-N'-(3,4-dichlorophenyl) urea | 72–77 | 11.4 | 11.8 | 25.3 | 25.8 | — | — |
| (4) N-methoxythio-N-methyl-N'-(2-fluorophenyl) urea | Oil | 13.9 | 13.9 | 8.3 | 8.3 | — | — |
| (5) N-norbornyloxythio-N-methyl-N'-(2-fluorophenyl) urea | Oil | 10.3 | 10.9 | 6.1 | 6.2 | — | — |
| (6) N-ethoxythio-N-methyl-N'-(2-fluorophenyl) urea | Oil | 13.1 | 13.6 | 7.8 | 7.9 | — | — |
| (7) N-propoxythio-N-methyl-N'-(2-fluorophenyl) urea | Oil | — | — | — | — | & 10.9 | & 11.1 |
| (8) N-isopropoxythio-N-methyl-N'-(2-fluorophenyl) urea | Oil | — | — | — | — | 10.9 | 11.2 |
| (9) N-ethoxythio-N-methyl-N'-(3,4-dichlorophenyl) urea | 60–61 | 10.9 | 10.9 | 24.1 | 24.0 | — | — |
| (10) N-isopropoxythio-N-methyl-N'-(3,4-dichlorophenyl) urea | Oil | 10.4 | 10.7 | 23.0 | 23.2 | — | — |
| (11) N-norbornyloxythio-N-methyl-N'-(3,4-dichlorophenyl) urea | Oil | 8.7 | 9.0 | 19.7 | 19.3 | — | — |
| (12) N-cyclohexyloxythio-N-methyl-N'-(2-fluorophenyl) urea | 69–72 | 10.7 | 10.8 | 6.4 | 6.5 | — | — |
| (13) N-octoxythio-N-methyl-N'-(2-fluorophenyl) urea | Oil | 9.8 | 9.7 | — | — | — | — |

*Carbon

TABLE II

| Compound | Herbicidal Effectiveness — Pre/Post | | | | | |
|---|---|---|---|---|---|---|
| | O | W | C | M | P | L |
| (1) | 98/100 | 98/100 | 95/80 | 100/100 | 100/100 | 100/100 |
| (2) | 40/93 | 85/100 | 93/93 | 90/100 | 100/100 | 100/100 |
| (3) | 95/100 | 100/100 | 100/85 | 100/100 | 100/100 | 100/100 |
| (4) | 100/100 | 100/100 | 80/100 | 100/100 | 100/100 | 100/100 |
| (5) | 100/100 | 100/100 | 95/100 | 100/100 | 100/100 | 100/100 |
| (6) | 100/100 | 100/100 | 96/65 | 100/100 | 100/100 | 100/100 |
| (7) | 100/100 | 100/100 | 90/70 | 100/100 | 100/100 | 100/100 |
| (8) | 100/100 | 100/100 | 100/90 | 100/100 | 100/100 | 100/100 |
| (9) | 75/90 | 100/100 | 100/85 | 100/100 | 100/100 | 100/100 |
| (10) | 90/100 | 100/100 | 100/90 | 100/100 | 100/100 | 100/100 |
| (11) | 45/100 | 100/100 | 95/95 | 100/100 | 100/100 | 100/100 |
| (12) | 100/100 | 100/100 | 100/100 | 100/100 | 100/100 | 100/100 |
| (13) | 70/93 | 95/93 | 100/93 | 100/93 | 100/95 | 100/99 |

O = Wild Oats (*Avena fatua*)
W = Watergrass (*Echinochloa crusgalli*)
C = Crabgrass (*Digitaria sanguinalis*)
M = Mustard (*Brassica arvensis*)
P = Pigweed (*Amaranthus retroflexus*)
L = Lambsquarter (*Chenopodium album*)

What is claimed is:

1. A method for controlling undesirable vegetation which comprises contacting the locus thereof with an herbicidally effective amount of the urea compound of the formula:

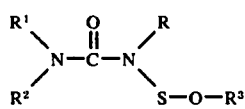

wherein R, R¹ and R² individually are hydrogen, alkyl of 1 to 6 carbon atoms, cycloalkyl or bicycloalkyl of up to 10 carbon atoms, alkoxy of 1 to 4 carbon atoms, carbocyclic mononuclear or binuclear aryl of 6 to 12 carbon atoms substituted with up to 2 fluorine, chlorine, bromine, nitro, trifluoromethyl or alkoxy of 1 to 4 carbon atoms; and R³ is alkyl of 1 to 10 carbon atoms, cycloalkyl or bicycloalkyl of up to 10 carbon atoms or carbocyclic mononuclear or binuclear aryl of 6 to 12 carbon atoms, substituted with up to 2 fluorine, chlorine, bromine, nitro, trifluoromethyl, or alkoxy of 1 to 4 carbon atoms.

2. An herbicidal composition comprising an herbicially effective amount of the compound of claim 1 admixed with a biologically inert carrier.

3. The method of claim 1 where R² is hydrogen.

4. The method of claim 1 wherein R² is hydrogen and R is alkyl of 1 to 6 carbon atoms.

5. The method of claim 1 where R² is hydrogen, R is alkyl of 1 to 6 carbon atoms and R¹ is alkyl of 1 to 6 carbon atoms, alkoxy of 1 to 4 carbon atoms or carbocyclic mononuclear or binuclear aryl of 6 to 12 carbon atoms substituted with up to 2 fluorine, chlorine, bromine, nitro, trifluoromethyl or alkoxy of 1 to 4 carbon atoms.

6. The method of claim 1 wherein R² is hydrogen, R is alkyl of 1 to 6 carbon atoms, and R¹ is phenyl, naphthyl, alkylphenyl of 7 to 12 carbon atoms, phenylalkyl of 7 to 12 carbon atoms, or phenyl, alkylphenyl or phenylalkyl substituted on the phenyl ring with 1 to 2 fluorine, chlorine, bromine, trifluoromethyl, nitro or alkoxy of 1 to 4 carbon atoms.

7. The method of claim 1 where R² is hydrogen, R is alkyl of 1 to 6 carbon atoms and R¹ is phenyl, alkylphenyl of 7 to 12 carbon atoms, or phenyl or alkylphenyl substituted with 1 to 2 fluorine, chlorine or bromine.

8. The method of claim 1 wherein R² is hydrogen, R is alkyl of 1 to 6 carbon atoms and R¹ is phenyl substituted with 1 to 2 fluorine or chlorine.

9. The method of claim 3 wherein R³ is alkyl of 1 to 6 carbon atoms or cycloalkyl or bicycloalkyl of up to 10 carbon atoms.

10. The method of claim 4 wherein R³ is alkyl of 1 to 6 carbon atoms or cycloalkyl or bicycloalkyl of up to 10 carbon atoms.

11. The method of claim 5 wherein R³ is alkyl of 1 to 6 carbon atoms or cycloalkyl or bicycloalkyl of up to 10 carbon atoms.

12. The method of claim 6 wherein R³ is alkyl of 1 to 6 carbon atoms or cycloalkyl or bicycloalkyl of up to 10 carbon atoms.

13. The method of claim 7 wherein $R^3$ is alkyl of 1 to 6 carbon atoms or cycloalkyl or bicycloalkyl of up to 10 carbon atoms.

14. The method of claim 8 wherein $R^3$ is alkyl of 1 to 6 carbon atoms or cycloalkyl or bicycloalkyl of up to 10 carbon atoms.

15. The method of claim 8 wherein $R^3$ is alkyl of 1 to 10 carbon atoms.

16. The method of claim 15 wherein R is methyl, $R^1$ is 3,4-dichlorophenyl or 2-fluorophenyl and $R^3$ is isopropyl or octyl.

17. The composition of claim 2 wherein $R^2$ is hydrogen.

18. The composition of claim 2 wherein $R^2$ is hydrogen and R is alkyl of 1 to 6 carbon atoms.

19. The composition of claim 2 wherein $R^2$ is hydrogen, R is alkyl of 1 to 6 carbon atoms and $R^1$ is alkyl of 1 to 6 carbon atoms, alkoxy of 1 to 4 carbon atoms or carbocyclic mononuclear or binuclear aryl of 6 to 12 carbon atoms substituted with up to 2 fluorine, chlorine, bromine, nitro, trifluoromethyl or alkoxy of 1 to 4 carbon atoms.

20. The composition of claim 2 wherein $R^2$ is hydrogen, R is alkyl of 1 to 6 carbon atoms, and $R^1$ is phenyl, naphthyl, alkylphenyl of 7 to 12 carbon atoms, phenylalkyl of 7 to 12 carbon atoms, or phenyl, alkylphenyl or phenylalkyl substituted on the phenyl ring with 1 to 2 fluorine, chlorine, bromine, trifluoromethyl, nitro or alkoxy of 1 to 4 carbon atoms.

21. The composition of claim 2 wherein $R^2$ is hydrogen, R is alkyl of 1 to 6 carbon atoms and $R^1$ is phenyl, alkylphenyl of 7 to 12 carbon atoms, or phenyl or alkylphenyl substituted with 1 to 2 fluorine, chlorine or bromine.

22. The composition of claim 2 wherein $R^2$ is hydrogen, R is alkyl of 1 to 6 carbon atoms and $R^1$ is phenyl substituted with 1 to 2 fluorine or chlorine.

23. The composition of claim 17 wherein $R^3$ is alkyl of 1 to 6 carbon atoms or cycloalkyl or bicycloalkyl of up to 10 carbon atoms.

24. The composition of claim 18 wherein $R^3$ is alkyl of 1 to 6 carbon atoms or cycloalkyl or bicycloalkyl of up to 10 carbon atoms.

25. The composition of claim 19 wherein $R^3$ is alkyl of 1 to 6 carbon atoms or cycloalkyl or bicycloalkyl of up to 10 carbon atoms.

26. The composition of claim 20 wherein $R^3$ is alkyl of 1 to 6 carbon atoms or cycloalkyl or bicycloalkyl of up to 10 carbon atoms.

27. The composition of claim 21 wherein $R^3$ is alkyl of 1 to 6 carbon atoms or cycloalkyl or bicycloalkyl of up to 10 carbon atoms.

28. The composition of claim 22 wherein $R^3$ is alkyl of 1 to 6 carbon atoms or cycloalkyl or bicycloalkyl of up to 10 carbon atoms.

29. The composition of claim 22 wherein $R^3$ is alkyl of 1 to 10 carbon atoms.

30. The composition of claim 29 wherein R is methyl, $R^1$ is 3,4-dichlorophenyl or 2-fluorophenyl and $R^3$ is isopropyl or octyl.

* * * * *